US00PP12927P2

(12) United States Plant Patent
Trees

(10) Patent No.: US PP12,927 P2
(45) Date of Patent: Sep. 10, 2002

(54) VERBENA PLANT NAMED 'BALWILROSE'

(75) Inventor: Scott Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 28 days.

(21) Appl. No.: 09/822,602

(22) Filed: Mar. 30, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named 'Balwilrose', characterized by its reddish purple flowers, mounded trailing habit, and dark green leaves.

2 Drawing Sheets

BACKGROUND OF THE INVENTION

The present invention comprises a new and distinct verbena plant, botanically known as *Verbena hybrida* and hereinafter referred to by the cultivar name 'Balwilrose'.

The new cultivar was developed by the inventor through a controlled breeding program during 1998, at Arroyo Grande, Calif. The objective of breeding program was the development of verbena cultivars with semi-trailing mounded habit, continuous flowering, excellent basal branching and small, dark green foliage.

The female (seed) parent of 'Balwilrose' was the proprietary verbena cultivar designated PAS984116 which exhibits a vigorous trailing growth habit, dark pink flowers and dark green foliage. The male (pollen) parent of 'Balwilrose' was the commercially available verbena, 'SUNVP-SU' (U.S. Plant Pat. No. 10,311), which exhibits a vigorous trailing growth habit, red flowers and dark green foliage.

Asexual reproduction of the new cultivar by terminal stem cuttings in Arroyo Grande, Calif. and West Chicago, Ill. has demonstrated that the characteristics of the new cultivar as herein described are firmly fixed and are retained through successive generations of such asexual propagation.

SUMMARY OF THE INVENTION

It was found that the cultivar of the present invention:

(a) Exhibits reddish purple flowers, (b) Forms dark foliage, (c) Exhibits a good basal branching character and (d) Exhibits a mounded and trailing growth habit.

When the new cultivar of the present invention is compared to its male parent, 'SUNVP-SU', it is found that the new cultivar has longer internodes, larger leaves, and larger flowers but fewer flowers per inflorescence as detailed in TABLE A.

BRIEF DESCRIPTION OF THE PHOTOGRAPHS

The accompanying photographs illustrate the overall appearance of the new cultivar as true as it is reasonably possible to obtain colored reproductions of this type. Color in the photographs may differ slightly from the color values cited in the detailed botanical description which accurately describe the actual colors of the new Verbena.

Sheet 1 depicts the growth habit of four plants of 'Balwilrose' grown in a pot for 12 weeks.

Sheet 2 depicts a close-up view of typical flowers of 'Balwilrose'. The plants were grown in a greenhouse at West Chicago, Ill., U.S.A.

DETAILED BOTANICAL DESCRIPTION

The 'Balwilrose' cultivar has not been observed under all posssible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Aug. 15, 2000. The readings were taken between 1:00 and 3:00 p.m. under natural daylight conditions. The plants used for the descriptions were produced from cuttings taken from stock plants and grown for about 11 weeks after planting rooted cuttings in 10 cm pots in a double poly carbonate covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balwilrose'.

Parentage:

*Female parent.*—Proprietary verbena cultivar PAS984116.

*Male parent.*—'SUNVP-SU'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8–10 weeks after the planting of a rooted cutting, commonly measures approximately 12 cm in height and approximately 35 cm in width.

*Form.*—Upright mounded and trailing.

*Stem.*—Tetragonal, approximately 1.4 mm in diameter, with dense short soft pubescence, 147B with some anthocyanin pigmentation, RHS 59A, along the edges. Internode length is approximately 3.5 cm.

*Foliage.*—Leaves are opposite, ovate with serrate to lobed margin, acute apex, attenuate to slightly oblique base. Texture: Velvety, covered with dense short soft hairs on upper surface and along veins on lower surface. Size: Approximately 3.2 cm in length and approximately 2.3 cm at widest point. Color: Upper surface is 137A, lower surface is 137C. Venation is reticulate, 145A on upper and lower surface. Petiole is 3 mm in length.

Flowering description:

*Flowering habit.*—Freely flowering.

*Natural flowering season.*—Spring through autumn.

*Inflorescence type.*—Corymb. Approximately 3.9 cm deep and approximately 5.6 cm in diameter with approximately 14 fully open flowers per inflorescence at any one time.

*Peduncle.*—Approximately 3 cm in length, 1.3 mm in diameter.

*Bud.*—Round, 9 mm in diameter, 82C.

*Petals.*—Five, fused at base, non-overlapping, flat.

*Flower.*—Diameter: Approximately 2.9 cm. Corolla tube length: Approximately 2.1 cm.

*Calyx.*—1.9 cm in length, 2 mm in diameter, 5 toothed, 5 ribbed, with stipules. Ribs and stipules are 143A, spaces between ribs are 144D (both surfaces).

*Flower color.*—Upper surface, fully opened: Venation of 70A, with intervenous spaces of 67A, base is 2D; Whiskers of 2D surround opening of corolla tube. Lower surface: Slightly redder than 75A.

*Reproductive organs.*—There are 4 stamens, one pistil 1.9 cm in length.

Seed production: Seed production has not been observed.

Disease resistance: Disease resistance has not been observed.

TABLE A

| CHARACTERISTIC | 'BALWILROSE' | 'SUNUP-SU' |
|---|---|---|
| INTERNODE LENGTH - CM | 3.5 | 2.1 |
| LEAF LENGTH × WIDTH - CM | 3.2 × 2.3 | 2.2 × 1.5 |
| FLOWER DIAMETER - CM | 2.9 | 1.5 |
| INFLORESCENCE LENGTH × WIDTH - CM | 3.9 × 5.6 | 3.9 × 4 |
| # FLOWERS/INFLORESCENCE | 14 | 25 |
| COROLLA TUBE LENGTH - CM | 21 | 1.7 |
| FLOWER COLOR - UPPER SURFACE - RHS | 67A with venation of 70A, base 2D | 44B at apex; 45A at base |

I claim:

1. A new and distinct cultivar of *Verbena hybrida* plant named 'Balwilrose' substantially as herein shown and described, which:

(a) Exhibits reddish purple flowers, (b) Forms dark green foliage, (c) Exhibits a good basal branching character and (d) Exhibits a mounded and trailing growth habit.

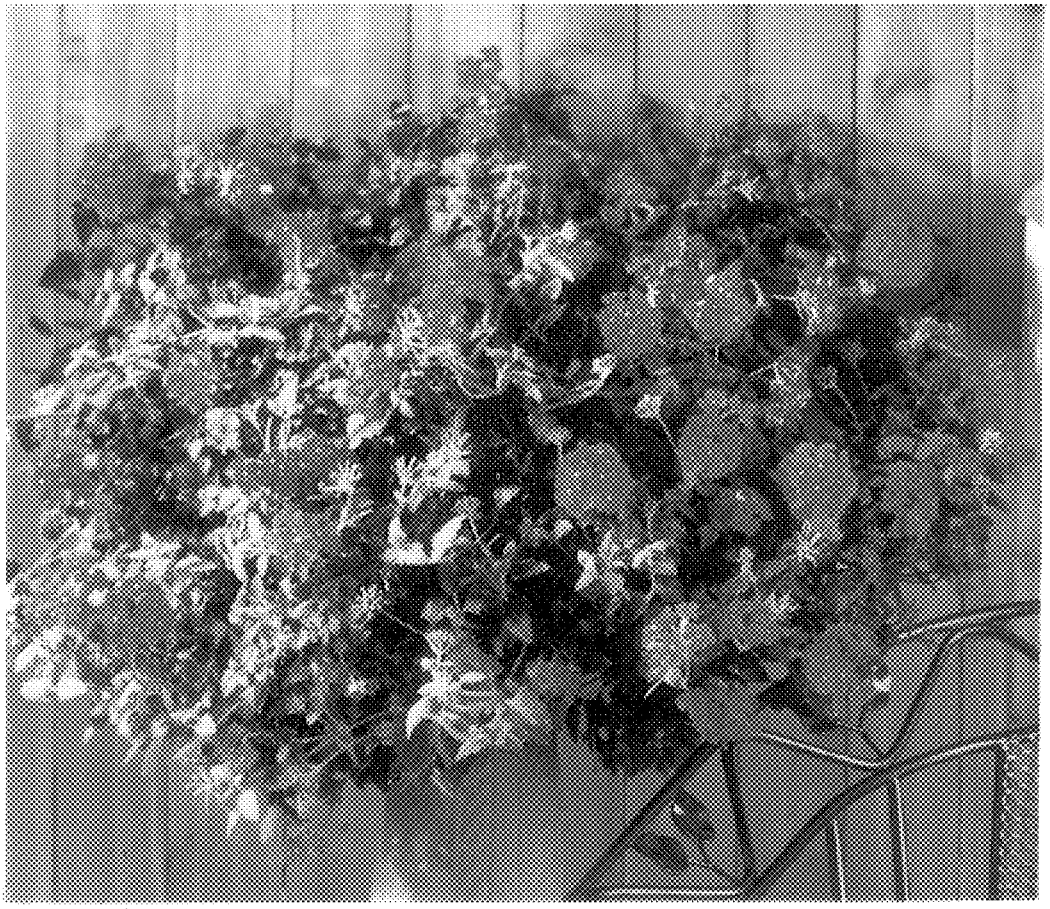

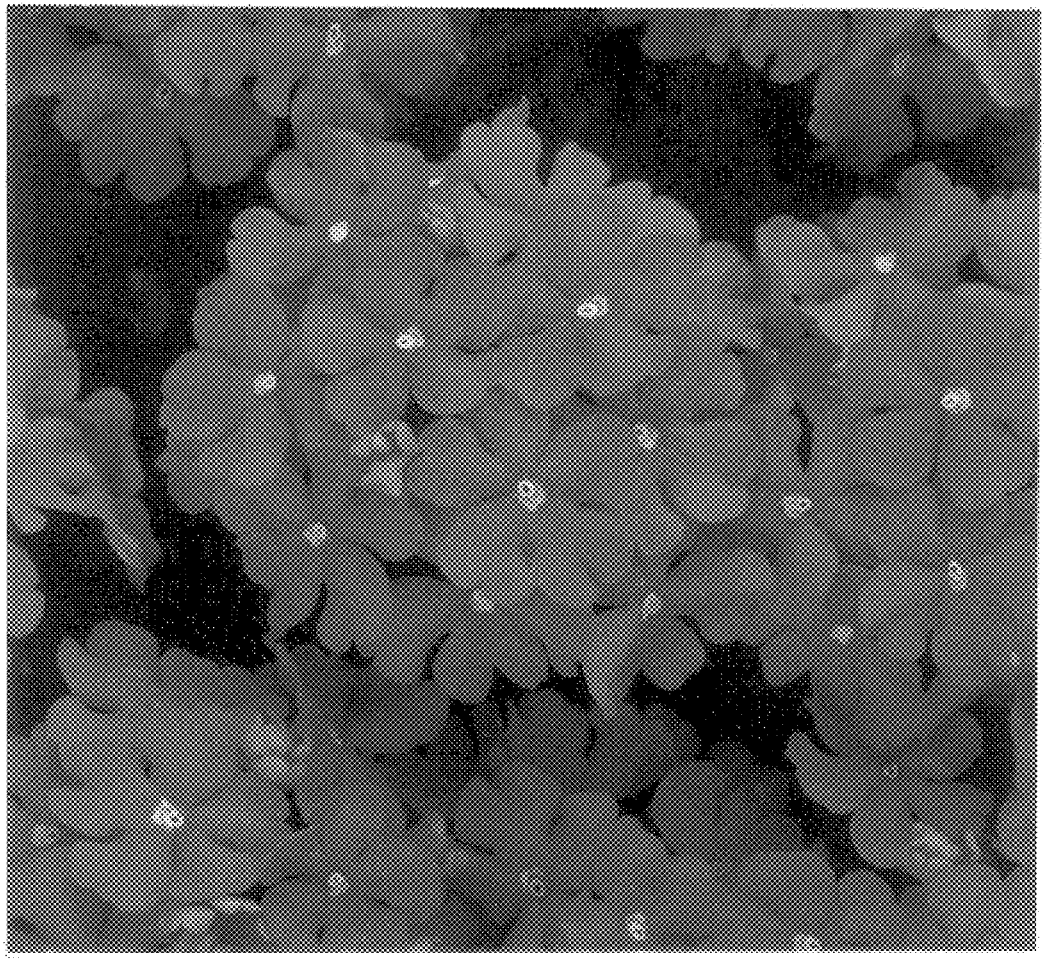

* * * * *